United States Patent [19]

Kato et al.

[11] 4,338,033

[45] Jul. 6, 1982

[54] DENSITOMETER

[75] Inventors: Yutaka Kato, Tamo; Ryo Fujimori, Hachiouji, both of Tokyo, Japan

[73] Assignee: Inoue-Japax Research Incorporated, Yokohama, Japan

[21] Appl. No.: 155,383

[22] Filed: Jun. 2, 1980

[30] Foreign Application Priority Data

Jun. 8, 1979 [JP] Japan .............................. 54-78001[U]

[51] Int. Cl.³ .......................... G01N 21/01; G01J 1/42
[52] U.S. Cl. .................................. 356/444; 346/33 A; 346/49; 356/223
[58] Field of Search ............... 356/432, 223, 434, 344, 356/444; 346/33 A, 1.1, 49

[56] References Cited

U.S. PATENT DOCUMENTS

| | | | |
|---|---|---|---|
| 3,706,877 | 12/1972 | Clifford, Jr. et al. ............... | 364/558 |
| 3,842,422 | 10/1974 | Vandenbroek et al. ........ | 356/432 X |
| 3,902,813 | 9/1975 | Vandenroek et al. .......... | 356/444 X |
| 4,005,434 | 1/1977 | Golias et al. ......................... | 346/1.1 |
| 4,116,565 | 9/1978 | Powell et al. .................... | 356/432 X |
| 4,118,781 | 10/1978 | Brezinski et al. ............... | 356/444 X |

Primary Examiner—John K. Corbin
Assistant Examiner—Bruce Y. Arnold
Attorney, Agent, or Firm—Karl F. Ross

[57] ABSTRACT

A densitometer comprising a recorder so adapted as to be capable of recording a set of analytical data obtained with a photometric system twice at a definite recording interval, an index arranged at a position apart by a distance equal to said recording interval from the recording pen of said recorder, a switch for setting boundary point and another switch commanding erasure of boundary point, said densitometer being so adapted as to permit setting and erasing boundary point by using the first recorded densitogram and said index.

1 Claim, 8 Drawing Figures

DENSITOMETER

BACKGROUND OF THE INVENTION (a) Field of the Invention

The present invention relates to a densitometer to be used for processing fractionated patterns of sera formed with electrophoretic apparatus.

(b) Description of the Prior Art

FIG. 1 shows a basic pattern of concentration distribution i.e., densitogram of a fractionated pattern formed by electrically energizing a carrier made of cellulose acetate film onto which man's serum is applied (a healthy man's serum generally shows this pattern). Such an electrophoretic pattern usually consists of five fractions of A, B, C, D and E including five peaks of $a_0$, $A_1$, $a_2$, $a_3$ and $a_4$ which correspond to albumin (A), alpha 1 globulin (B), alpha 2 globulin (C), beta globulin (D) and gamma globulin (E) respectively. Diagnosis or distinguishment between normality and abnormality is done on the basis of an analog pattern and percentages of integrals of the individual fractions relative to that of the entire pattern. However, patterns of concentration distribution on fractionated patterns of actual samples may include peaks produced by various causes in addition to those illustrated in FIG. 1. The pattern shown in FIG. 2, for example, has a peak designated as $a_5$ in addition to the abovementioned five peaks and consists of six fractions showing a boundary point $b_5$ in addition to the regular boundary points of $b_1$, $b_2$, $b_3$ and $b_4$. The boundary point $b_5$ is formed depending on freshness of the serum due to a certain component of the serum, namely $beta_{1c}$ globulin which is fractionated by the electrophoresis. Further, the pattern shown in FIG. 3 has no boundary point corresponding to $b_4$, and consists of only four fractions having boundary points of $b_1$, $b_2$ and $b_3$.

In case where a sample produces a pattern consisting of six or more fractions including peak(s) in addition to the five basic ones shown in FIG. 1 or consisting of four fractions, inconvenience is caused in automatic processing of colorimetric data with a computer. FIG. 4 shows an example of a configuration of a densitometer and a photometric apparatus which are currently used. In the block diagram shown in FIG. 4, the light emitted from a light source 3 is passed through a lens 4, a filter 5 and a slit 6, used for irradiating a carrier 1 and detected with a photo detector element 7. The carrier 1 has fractionated patterns of sera 2, 2', 2''. . . formed thereon as shown in FIG. 5, and is placed between the light source and the photo detector for photometry of the individual fractionated patterns while scanning in the direction perpendicular to the shifting direction of the carrier. That is to say, the light emitted from the light source and passing through the sample (fractionated pattern of a serum) is received by the photo detector element 7, whose output corresponding to sample concentration is amplified with a preamplifier 8, converted by a logarithmic converter 9 into logarithmic values for preparing an analog densitogram as shown in FIG. 1 and so on. Successively, outputs from the logarithmic converter 9 are inputted into an A/D converter 10 and converted into digital signals at definite time intervals by operating a conversion command signal generator 11 with photometry commands 11a from a computer 12. On the basis of the digital data obtained at this stage, percentage of integral of each fraction relative to that of the entire pattern is determined.

In the operations described above, it is possible to determine the boundary points by calculating minimum values in case of a densitogram traced based on an electrophoretic pattern consisting of five fractions as exemplified in FIG. 1. In case of a densitogram consisting of more than five fractions as shown in FIG. 2, however, it was impossible to determine the regular five fractions and calculate integrals, etc. of the individual fractions. Further, in case of a densitogram consisting of four fractions as shown in FIG. 3, it was also impossible to determine the regular five fractions and calculate integrals, etc. of the individual fractions. Therefore, it is required for the inspector to check analog densitograms and electrophoretic patterns, divide a densitogram into five fractions of those of albumin, alpha 1 globulin, alpha 2 globulin, beta globulin and gamma globulin and then perform data processing for recalculation.

In order to determine the regular five fractions of densitograms such as those illustrated in FIG. 2 and FIG. 3 and calculate data such as percentages of integrals of the individual fractions relative to that of the entire densitogram, there has conventionally been used a system described below. A carrier on which samples showing six fractions and four fractions as described above is fed into a densitometer which is separate from a general type of densitometer. The former densitometer is equipped with a photometric system which has the same construction as that shown in FIG. 4 and performs photometry of the samples once again. The densitometer is equipped with a recorder as shown in FIG. 6 which records photometric results on a recording chart paper 21 on a recorder of a densitometer 20 with a recorder pen 22. The densitometer comprises an electric circuit shown in FIG. 7 which consists of an amplifier 25, a logarithmic converter 26, an A/D converter 27, an operation circuit 28 and a D/A converter 29, and records output signals from the D/A converter produced on the basis of the output detected by the photo detector element 7 of the photometric system by operating the recording pen of the recorder shown in FIG. 6. On the other hand, locations corresponding to minimum values (valleys) are determined as boundary points by a boundary point detector 30 arranged in the operation circuit and percentages of integrals of the fractions between the individual pairs of neighboring boundary points relative to that of the entire densitograms are calculated. In FIG. 6, the reference numeral 24 represents boundary buttons which are connected to the boundary point detector 30. Out of these buttons, the "+" pushbutton 24a is so adapted as to set, upon depression thereof, a boundary point for calculation. Speaking more specifically, a section from a position on a densitogram being traced by the recorder pen at the moment of depressing the pushbutton to the next boundary point is determined as a fraction for calculation. It is therefore possible to obtain data on the regular five fractions by depressing the pushbutton at a point which is regarded as corresponding to the fourth boundary point such as $b'_4$ on a densitogram having four fractions as shown in FIG. 3. Though a densitogram having low slopes is shown in FIG. 3, a densitogram actually consists of fine irregular convexities and concavities. It is therefore possible for an inspector to visually judge the fourth boundary point on a densitogram. The "−" pushbutton 24b is arranged to ignore a valley to be processed as a boundary point when being depressed. In case of a densitogram consisting of six or more fractions as shown in FIG. 2, $b_5$ is not processed as a boundary point by depressing the pushbutton 24b at the position of $b_5$ on the densitogram shown in this drawing. That is to say, the pushbutton 24b makes it possible to calculate and record data on the regular five fractions corresponding to A, B, C, D and E shown in FIG. 1.

For determining the fractions with such a conventional system, it is necessary to depress the pushbutton 24a or 24b the moment that the recorder pen just reaches the point $b_5$ in FIG. 2 or point $b'_4$ in FIG. 3 while a densitogram is being recorded with the recorder pen 22. The timing to depress the boundary buttons to determine a point to be processed as a boundary point and erase a valley to be ignored as a boundary point must be judged momentarily depending on subjective sense of the operator. Therefore, the pushbuttons are often depressed before and after correct boundary points, thereby causing errors in analytical data in practice.

SUMMARY OF THE INVENTION

A general object of the present invention is to provide a densitometer equipped with a recorder capable of successively recording two densitograms of one and the same sample and so adapted as to permit obtaining a correct densitogram consisting of the regular five fractions by depressing boundary buttons at positions judged on a densitogram being recorded with a recorder pen using a corresponding densitogram traced for the first time as reference.

DETAILED DESCRIPTION OF THE PREFERRED EMBODIMENT

Figure 1:
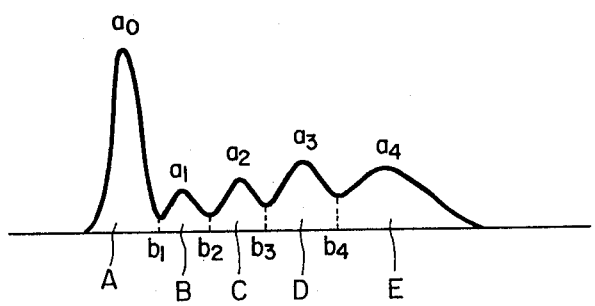
FIG. 1 shows a graph illustrating a densitogram having normal five fractions.
Figure 2:
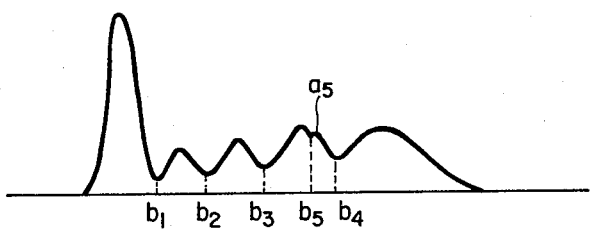
FIG. 2 shows a graph illustrating an example of a densitogram consisting of six fractions.
Figure 3:
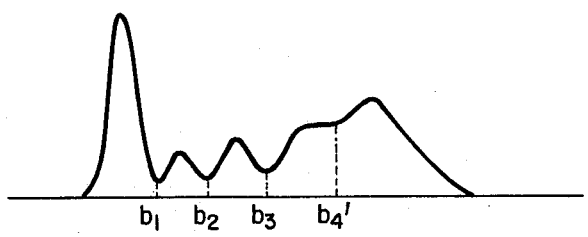
FIG. 3 shows a graph illustrating a densitogram consisting of four fractions.
Figure 4:
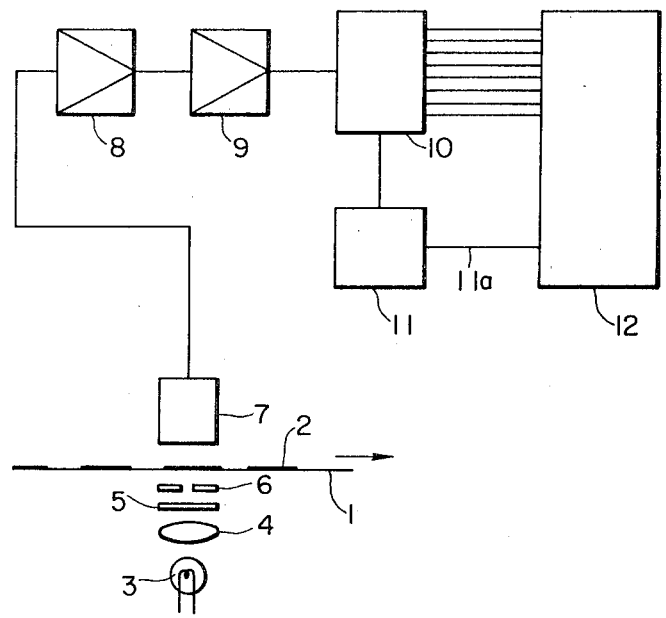
FIG. 4 shows a block diagram illustrating a combination of a photometric system for carrying out photometry of electrophoretic patterns and a data processing circuit.
Figure 5:
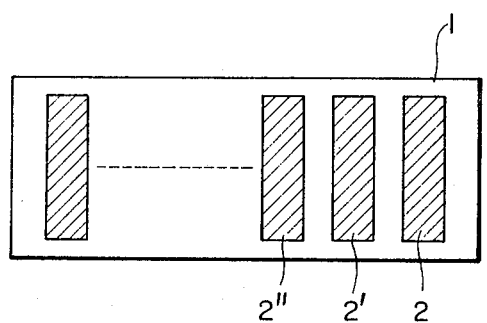
FIG. 5 shows a diagram illustrating positions of samples applied onto a carrier.
Figure 6:
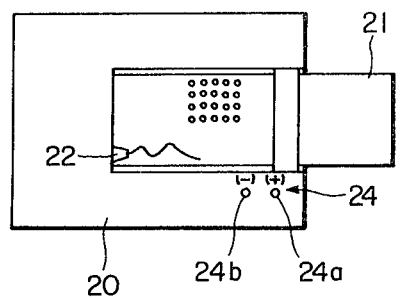
FIG. 6 shows a diagram illustrating the conventional recorder for densitometers so adapted as to permit determining boundary points and erasing boundary points.
Figure 7:
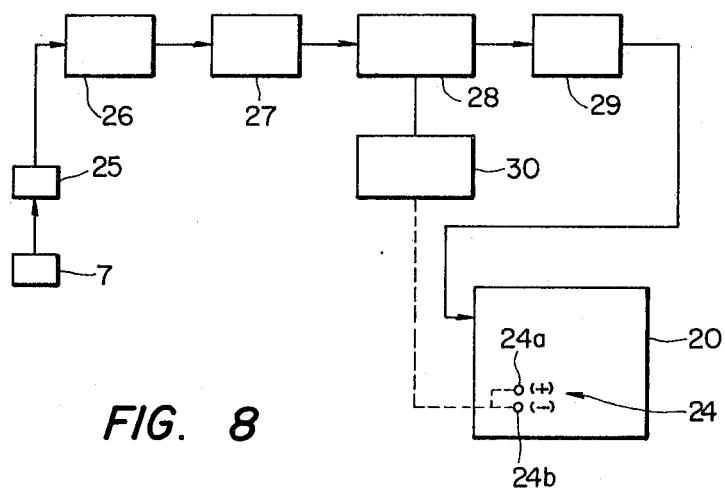
FIG. 7 shows a block diagram illustrating an electric circuit used in the densitometer equipped with the recorder shown in FIG. 6.
Figure 8:
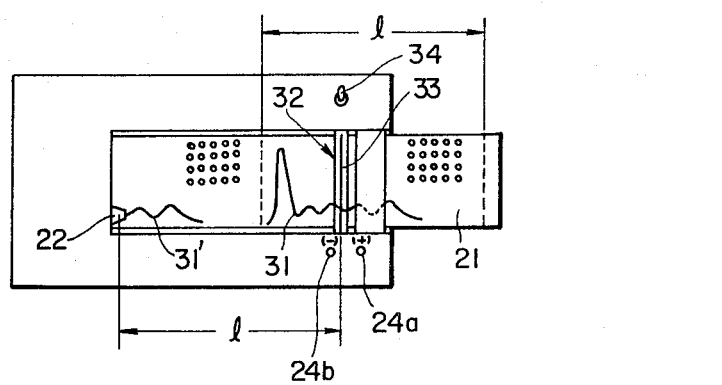
FIG. 8 shows a diagram illustrating the recorder used for the densitometer according to the present invention.

FIG. 8 shows a plan view of the densitometer according to the present invention which records densitograms on the recording chart paper 21 with the recording pen 22 in the same manner as the conventional recorder shown as the conventional example in FIG. 6 on the basis of data obtained with the photometric system illustrated in FIG. 4. The recorder of the densitometer according to the present invention is, however, so adapted as to record a densitogram 31' which is quite the same as that represented by the reference numeral 31 at a definite interval on the recording chart paper unlike the conventional recorder shown in FIG. 6. The reference numeral 32 designates an index which is arranged over the recording chart paper so as not to hinder shifting thereof, but permit observing an index line 33 overlapped with the densitogram. Further, the distance as measured from the reference line of the index of the recording pen 22 is set equal to the recording chart paper length required for recording a densitogram. Therefore, the point indicated by the index on the first densitogram 31 traced on the recording chart paper precisely corresponds to the point of the second densitogram 31' being traced with the recording pen. The reference numeral 34 denotes a selector switch which permits selecting whether or not a densitogram is to be recorded once or twice repeatedly. The other members of the recorder are substantially the same as those of the conventional recorder shown in FIG. 6 and will not be described specifically.

In order to process electrophoretic data with the densitometer described above, the operator judges a point to be processed as a boundary point (or a valley to be erased) which is preliminarily known on the first densitogram 31 and depresses the boundary pushbutton switch 24a (or 24b) the moment that said point becomes coincident with the reference line of the index. By this operation, a point being traced with the recording pen on the second densitogram is processed as a boundary point and the fraction terminating at the next boundary point (a valley is determined automatically as a boundary point by the densitometer) can be measured correctly. In case of a boundary point to be erased (a valley to be ignored), the operator depresses the pushbutton 24b before the boundary point becomes coincident with the reference line, whereby the boundary point is erased and ignored by the densitometer.

As is understood from the foregoing descriptions, the densitometer according to the present invention permits preliminarily judging points to be adopted as boundary points and erased on a densitogram of a sample recorded in the first place, and setting and erasing boundary points the moment that said points are overlapped with the reference line, thereby making it possible to perform densitometric operations easily and accurately.

We claim:

1. A densitometer comprising a recorder so adapted as to be capable of recording two analog densitograms on the basis of a single set of analytical data at a definite recording interval, an index arranged at a position apart by a distance equal to said recording interval from the recording pen of said recorder, a first pushbutton for setting boundary point on said analog densitogram recorded for the second time and a second pushbutton for commanding erasure of boundary point on said analog densitogram, said densitometer being so adapted as to process analytical data while processing a point as a boundary point when the first pushbutton is depressed the moment that said point becomes coincident with said index and while erasing a valley on said densitogram traced for the second time when said second pushbutton is depressed before said valley on the first densitogram becomes coincident with said index.

* * * * *

UNITED STATES PATENT AND TRADEMARK OFFICE
CERTIFICATE OF CORRECTION

PATENT NO. : 4,338,033
DATED : July 6, 1982
INVENTOR(S) : Yutaka KATO and Ryo FUJIMORI It is certified that error appears in the above-identified patent and that said Letters Patent is hereby corrected as shown below:

On The Title Page

Item [73] read Inoue-Japax Research Incorporated, Yokohama, Japan" as --OLYMPUS OPTICAL CO., LTD., Tokyo, Japan--

Attorney, Agent or Firm, read "Karl F. Ross" as --CUSHMAN, DARBY & CUSHMAN--

Signed and Sealed this

Sixteenth Day of October 1984

[SEAL]

Attest:

GERALD J. MOSSINGHOFF

Attesting Officer

Commissioner of Patents and Trademarks